United States Patent [19]

Tennigkeit et al.

[11] Patent Number: 5,006,127
[45] Date of Patent: * Apr. 9, 1991

[54] AGENT FOR THE OXIDATIVE DYEING OF HAIR, METHOD FOR THE PREPARATION OF THE AGENT AND USE OF THE AGENT

[75] Inventors: Jürgen Tennigkeit, Seeheim; Herbert Lorenz, Gross-Bieberau, both of Fed. Rep. of Germany

[73] Assignee: Goldwell GmbH, Darmstadt-Eberstadt, Fed. Rep. of Germany

[*] Notice: The portion of the term of this patent subsequent to Oct. 11, 2005 has been disclaimed.

[21] Appl. No.: 187,029

[22] PCT Filed: Aug. 19, 1987

[86] PCT No.: PCT/EP87/00465
§ 371 Date: Apr. 14, 1988
§ 102(e) Date: Apr. 14, 1988

[87] PCT Pub. No.: WO88/01161
PCT Pub. Date: Feb. 25, 1988

[30] Foreign Application Priority Data

Aug. 21, 1986 [DE] Fed. Rep. of Germany ....... 3628397

[51] Int. Cl.$^5$ ............................................... A61K 7/13
[52] U.S. Cl. ........................................ 8/406; 8/405; 8/407; 8/408; 8/431; 8/634; 8/635; 132/204; 424/71
[58] Field of Search ................... 8/405, 406, 407, 408, 8/431, 618, 634, 635; 424/71; 132/204

[56] References Cited

U.S. PATENT DOCUMENTS

| | | | |
|---|---|---|---|
| 1,677,508 | 7/1928 | Winogradoff | 8/634 |
| 2,934,396 | 4/1960 | Charle et al. | 8/423 |
| 4,010,872 | 3/1977 | Lozano et al. | 8/405 |
| 4,630,621 | 12/1986 | Pontani | 132/204 |
| 4,776,856 | 10/1988 | Tennigkeit et al. | 8/406 |
| 4,804,385 | 2/1989 | Grollier et al. | 8/423 |
| 4,808,190 | 2/1989 | Grollier et al. | 8/423 |

FOREIGN PATENT DOCUMENTS 2028818 12/1970 Fed. Rep. of Germany.
2185498 7/1987 United Kingdom.

Primary Examiner—Paul Lieberman
Assistant Examiner—Linda D. Skaling

[57] ABSTRACT

In a method for the oxidative dyeing of human or animal hair a hair dyeing agent is prepared from at least one oxidation dye in creme or gel form, which is adjusted to a pH of 5.9 to 6.9.

The preparation is performed with the addition of at least one alkali metal salt or alkaline earth metal salt as catalyst, which is added simultaneously with or immediately after the mixing of the oxidation dye with the oxidizing agent, the amount added being such that it is contained in the treatment-ready hair dyeing agent in proportions between 0.0001 and 1.00 wt.-%, preferably between 0.0004 and 0.001 wt.-%.

10 Claims, No Drawings

AGENT FOR THE OXIDATIVE DYEING OF HAIR, METHOD FOR THE PREPARATION OF THE AGENT AND USE OF THE AGENT

The invention relates to an agent for the oxidative dyeing of human and animal hair, which is prepared immediately before application by mixing with an oxidant a dye in creme or gel form containing at least one oxidation dye, and adjusting it to a pH between 5.9 and 6.9. The invention furthermore concerns a method for preparing the agent, and its use.

Until recent times use has been made, for the permanent coloring of human hair, of dyes in gel or creme form containing alkaline oxidation dyes, which are mixed immediately before use with an acid oxidant, e.g., hydrogen peroxide, to form the ready-to-use hair dye that is to be applied to the hair. The coloring is developed in this case by the reaction of certain developer substances with certain coupler substances in the presence of a suitable oxidant. The preparation when ready for application is in this case definitely in the alkaline range, so that the surfaces of the hairs are treated in a manner that is advantageous for the penetration of the oxidation dyes. On the other hand, alkaline preparations also stress the hair, so that, especially in the case of repeated treatment, e.g., repeated redyeing, damage can be done to the hair. Such redyeing, however, especially in the case of light-colored hair, is necessary in order, for example, to match the color of undyed regrowth hair to the previously dyed lengths of hair, and to refresh the color of previously dyed lengths of hair when they have been faded or bleached in the course of time by external effects such as exposure to sunlight, frequent washing, and the like.

Earlier attempts to avoid the effects of alkaline hair dyes especially on the ends of the hair by acidifying the ready-to-apply preparation made from the oxidation dye and the oxidant, have resulted in an unsatisfactory coloring action of the agent. Not until recent times has the applicant developed an agent that is in the weakly acid range (pH between 5.9 and 6.9) in the ready-to-apply state, which produces a good coloring of the hair, while the damage to the hair that has been observed with alkaline hair dyes is largely avoided (patent application P 35 30 270.4). This surprising result is achieved in this hair dye by the addition of small amounts of manganese dioxide which apparently acts as a catalyst of the dyeing action The invention is addressed to the problem of devising an agent for the oxidative dyeing of hair and a method for its preparation, which, while further improving the dyeing action, will not lead, even when repeatedly used, to the hair damage observed in the use of alkaline hair dyes.

Setting out from a hair dye of the kind described above, this problem is solved according to the invention in that it additionally contains at least one alkali metal salt and/or alkaline earth metal salt, the salt or salts being preferably from the group containing potassium iodide, potassium bichromate, lithium chloride, magnesium acetate, calcium chloride and barium nitrate.

It has been found that the alkali metal salt and/or alkaline earth metal salt in the hair dyeing agent when ready for application leads to the desired catalytic intensification of the coloring action when it is contained in amounts between 0.0001 and 1.00 weight-percent, preferably between 0.0004 and 0.001 weight-percent. In the hair dyeing agent according to the invention, a content of the alkali metal salts or alkaline earth metal salts suffices which is one to two powers of ten less than it is in the above-mentioned newly developed acidified hair dyeing agents acting with manganese dioxide powder as catalytic additive.

In the preparation of the hair dyeing agent according to the invention, either the alkali metal salt or alkaline earth metal salt is mixed with the oxidation dye before the addition of the, as a rule, liquid oxidant, or it can also be added together with or immediately after the oxidation dye is mixed with the oxidant.

When the hair dyeing agent according to the invention is used for dyeing human hair, the procedure is virtually the same as it has been with alkaline hair dyeing agents. Immediately before use, the ready-to-apply hair dyeing agent is prepared from at least one dye in creme or gel form containing one oxidation dye plus the alkali or alkaline earth metal salt, by adding the oxidant; it is applied to the hair and allowed to act for a given period of time, whereupon the hair dyeing agent is washed out. It has been found that outstandingly persistent coloring of human hair in brilliant color tones are thus made possible, unless darker hair is to be recolored to a lighter shade The hair damage that is to be attributed to the alkalinity of the hair dyes predominantly used today are at the same time completely prevented.

To brighten or lighten the coloring of darker hair, it is necessary to resort to the known alkaline hair dyes Since the damage to hair by such alkaline hair dyes, however, does not, as a rule, occur until after repeated recoloring, such damage can be avoided in recoloring by first applying a known alkalinized hair dye to the darker regrown lengths of the hair close to the scalp and then applying the weakly acid hair dye to the adjoining, previously dyed hair lengths, whereupon both the alkaline and the weakly acid hair dyes are washed out of the treated hair after a sufficient period of time.

Particularly problematical with regard to hair damage is a combined permanent wave and hair dyeing treatment. The danger of hair damage is substantially reduced by using the hair dyeing agent according to the invention, in which case the procedure is first to allow a permanent wave preparation to act for a given period of time on the washed hair put up in curlers and then wash it out; the wound hair is then pre-fixed with a liquid oxidizing fixer and then, after removing the curlers, it is re-fixed with the weakly acid hair dye by allowing the latter to act on the hair for a period of time needed for the sufficient coloring of the hair, and then washing it out. The hair dyeing agent therefore replaces the fixer commonly used in permanent waving for the second fixing, i.e., it is used for a dual purpose, so to speak, and this prevents the damage otherwise to be feared in the use of alkalinized hair dyes.

The above-described possibilities for the use of the hair dyeing agent according to the invention will be further explained below with the aid of a series of special examples. Formulas will be described for hair dyeing agents prepared with the addition of potassium iodide as examples of the effectiveness of alkali metal salts, and of hair dye preparations made with magnesium acetate as examples of the effectiveness of alkaline earth metal salts.

EXAMPLE 1a

Oxidation Dyeing 20 ml of dye paste of the formula given below for the color, "hazelnut blond," with the addition of 0.0004% of potassium iodide was mixed with 40 ml of a developer solution containing 2% of $H_2O_2$, resulting in a hair dye with a pH of 6.8. The dye was applied to a medium heavy hair with a medium ash blond basic tone and allowed to work for 20 minutes.

The result was a recoloring of the hair to an intense hazelnut blond shade.

Experiments have shown that the time of action of the hair dye can amount to from 5 to 20 minutes, depending on the desired color intensity.

| Formula for "Hazelnut Blond" Dye Paste | |
|---|---|
| Cetylstearyl alcohol | 10.0 g |
| Coconut fatty acid monoethanolamide | 2.0 g |
| Stearic acid monoethanolamide | 2.0 g |
| Stearic acid diethanolamide | 1.0 g |
| p-Toluylenediamine sulfate | 0.25 g |
| m-Aminophenol | 0.01 g |
| Resorcinol | 0.01 g |
| p-Aminophenol | 0.08 g |
| p-Amino-o-cresol | 0.06 g |
| Picraminic acid | 0.05 g |
| Monoethanolamine | 0.2 g |
| Ammonium chloride | 0.2 g |
| Sodium lauryl sulfate | 0.3 g |
| Potassium iodide | 0.0004 g |
| Sodium sulfite | 0.25 g |
| Ethylenediaminetetraacetic acid | 0.2 g |
| Perfume | 0.2 g |
| Softened water to make | 100.00 g |

EXAMPLE 1b

Oxidation Dyeing 20 ml of paste dye of the formula given below for the color, "copper blond," with the addition of 0.0004% potassium iodide, was mixed with 40 ml of a developer solution containing 2% $H_2O_2$, resulting in a hair dyeing agent with a pH of 6.8.

The dye was applied to a medium-heavy hair with a basic medium ash blond shade and allowed to work for 20 minutes. As a result the color of the hair was changed to a subdued copper shade.

The time of action of the hair dye can amount to 5 to 30 minutes according to the desired final intensity of the color.

| Formula for the "Copper Blond" Paste Dye | |
|---|---|
| Cetylstearyl alcohol | 10.0 g |
| Coconut fatty acid monoethanolamide | 2.0 g |
| Stearic acid monoethanolamide | 2.0 g |
| Stearic acid diethanolamide | 1.0 g |
| p-Toluylenediamine sulfate | 0.20 g |
| p-Aminophenol | 0.70 g |
| p-Amino-o-cresol | 0.70 g |
| Monoethanolamine | 0.2 g |
| Ammonium chloride | 0.2 g |
| Sodium lauryl sulfate | 0.3 g |
| Potassium iodide | 0.0004 g |
| Sodium sulfite | 0.12 g |
| Ethylenediaminetetraacetic acid | 0.2 g |
| Perfume | 0.20 g |
| Softened water to make | 100.00 g |

EXAMPLE 2

Oxidation Dyeing for the Gentle, Acid Touch-Up of the Hair Tips after Normal Alkaline Dyeing 20 ml of the paste dye of the formula given in Example 1a for the color, "Hazelnut Blond," containing 0.0004% of potassium iodide was mixed with 40 ml of a developer solution containing 2% of $H_2O_2$, resulting in a hair dye with a pH of 6.8.

The dye was applied to a medium-heavy hair which had been of a hazelnut blond color and the lengths and tips of which are faded and have a light ash blond shade, and it was allowed to work for 10 minutes.

The result was a hazelnut blond color on the faded lengths and tips which matched the rest of the hair. The time of action of the preparation can again vary between 5 and 15 minutes according to the color intensities to be matched

EXAMPLE 3a

Oxidation Dyeing Combined with Permanent Waving

A permanent wave was given to a medium-heavy hair which had a natural dark gold blond color and in which the hair lengths and tips were faded.

The permanent wave was prepared according to instructions, up to and including the first fixing on the curlers.

For the second fixing and simultaneous dyeing, the curlers were removed and 20 ml of paste dye of the formula given below for the color "Cyclamen" containing 0.0004% of potassium iodide was mixed with 40 ml of a permanent-wave fixer with a hydrogen peroxide content of 2%.

The resultant hair dye with a pH of 6 8 was then applied to the hair with an applicator bottle and a sponge and allowed to act for 10 minutes. The result was that, in addition to the permanent wave, the color of the hair was changed to a reddish-violet (cyclamen) color shade. Depending on the desired color intensity, the time of action can be varied between 5 and 15 minutes.

| Formula for "Cyclamen" Paste Dye | |
|---|---|
| Cetyl stearyl alcohol | 10.0 g |
| Coconut fatty acid monoethanolamide | 2.0 g |
| Stearic acid monoethanolamide | 2.0 g |
| Stearic acid diethanolamide | 1.0 g |
| p-Toluylenediaminesulfate | 0.5 g |
| p-Amino-o-cresol | 0.4 g |
| p-Aminophenol | 0.1 g |
| Monoethanolamine | 0.2 g |
| Ammonium chloride | 0.2 g |
| Sodium lauryl sulfate | 0.3 g |
| Potassium iodide | 0.0004 g |
| Sodium sulfite | 0.25 g |
| Ethylenediaminetetraacetic acid | 0.2 g |
| Perfume | 0.2 g |
| Softened water to make | 100.00 g |

EXAMPLE 3b

Oxidation Dyeing Combined with Permanent Waving

A permanent wave was given to medium-heavy hair which had a natural tone of dark gold blond, in which hair lengths and ends were faded.

The permanent wave was performed according to the instructions for use up to and including the first fixing on the curler.

For the second fixing and simultaneous dyeing, the curlers were removed and 20 ml of paste dye of the formula given below for the color, "Mahogany," containing 0.0004 g of potassium iodide was mixed with 40 ml of a permanent wave fixer with a hydrogen peroxide content of 2%

The resultant hair dye with a pH of 6.8 was then applied to the hair with an applicator bottle and sponge and allowed to act for 10 minutes. As a result, in addition to the permanent wave, the hair color had been changed to a rich red tone. Depending on the desired intensity of the color the time of action can be varied between 5 and 15 minutes.

| Formula for the "Mahogany" Paste Dye | |
|---|---|
| Cetyl stearyl alcohol | 10.0 g |
| Coconut fatty acid monoethanolamide | 2.0 g |
| Stearic acid monoethanolamide | 2.0 g |
| Stearic acid diethanolamide | 1.0 g |
| p-Toluylenediamine sulfate | 0.4 g |
| p-Aminophenol | 0.4 g |
| p-Amino-o-cresol | 0.4 g |
| o-Nitro-p-phenylenediamine | 0.4 g |
| Monoethanolamine | 0.2 g |
| Ammonium chloride | 0.2 g |
| Sodium lauryl sulfate | 0.3 g |
| Potassium iodide | 0.0004 g |
| Sodium sulfite | 0.25 g |
| Ethylenediaminetetraacetic acid | 0.2 g |
| Perfume | 0.2 g |
| Softened water to make | 100.00 g |

EXAMPLE 4a

Oxidation Dyeing 20 ml of a paste dye of the formula given below for the color, "Hazelnut Blond," with the addition of 0.0006% of magnesium acetate, was mixed with 40 ml of a developer solution containing 2% $H_2O_2$, resulting in a hair dye with a pH of 6.8. The dye was applied to a medium-heavy hair with a medium ash blond basic tone, and allowed to work for 20 minutes.

The result was a recoloring of the hair to an intense hazelnut blond tone.

The working time can be between 5 and 20 minutes according to the desired color intensity.

| Formula of the "Hazelnut Blond" Paste Dye | |
|---|---|
| Cetylstearyl alcohol | 10.0 g |
| Coconut fatty. acid monoethanolamide | 2.0 g |
| Stearic acid monoethanolamide | 2.0 g |
| p-Toluylenediamine sulfate | 0.25 g |
| m-Aminophenol | 0.01 g |
| Resorcinol | 0.01 g |
| p-Aminophenol | 0.08 g |
| p-Amino-o-cresol | 0.06 g |
| Picraminic acid | 0.05 g |
| Monoethanolamine | 0.2 g |
| Ammonium chloride | 0.2 g |
| Sodium lauryl sulfate | 0.3 g |
| Magnesium acetate | 0.0006 g |
| Sodium sulfite | 0.25 g |
| Ethylenediaminetetraacetic acid | 0.2 g |
| Perfume | 0.2 g |

EXAMPLE 4b

Oxidation Dyeing 20 ml of paste dye of the formula given below for the color, "Copper Blond" with the addition of 0.0006% magnesium acetate, was mixed with 40 ml of a developer solution containing 2% of $H_2O_2$, resulting in a hair dye with a pH of 6.8.

The dye was applied to a medium-heavy hair with a medium ash blond basic tone and allowed to act for 20 minutes.

The result was a recoloring of the hair to a subdued copper tone.

Experiments showed that the time for which the hair dye acts can be varied between 5 and 30 minutes according to the resulting color intensity desired.

| Formula of the "Copper Blond" Paste Dye | |
|---|---|
| Cetyl stearyl alcohol | 10.0 g |
| Coconut fatty acid monethanol amide | 2.0 g |
| Stearic acid monoethanol amide | 2.0 g |
| Stearic acid diethanol amide | 1.0 g |
| p-Toluylenediamine sulfate | 0.20 g |
| p-Aminophenol | 0.70 g |
| p-Amino-o-cresol | 0.70 g |
| Monoethanolamine | 0.2 g |
| Ammonium chloride | 0.2 g |
| Sodium lauryl sulfate | 0.3 g |
| Magnesium acetate | 0.0006 g |
| Sodium sulfite | 0.12 g |
| Ethylenediaminetetraacetic acid | 0.2 g |
| Perfume | 0.2 g |
| Softened water to make | 100.00 g |

EXAMPLE 5

Oxidation Dyeing for Gentle, Acid Touch-Up of Hair Ends After Normal, Alkaline Initial Dyeing 20 ml of the paste dye of the formula given in Example 4a for the color, "Hazelnut Blond," with the addition of 0.0004% of magnesium acetate, was mixed with 40 ml of a developer solution containing 2% of $H_2O_2$, resulting in a hair dye with a pH of 6.8.

The dye was applied to a medium-heavy hair which had been dyed hazelnut blond and whose lengths and ends are faded and have a light ash blond tone, and it was allowed to work for 10 minutes.

The result was a hazelnut blond toning of the faded lengths and ends to match the original dye. The time the preparation is allowed to act can be between 5 and 15 minutes depending on the color intensities that are to be evened out.

EXAMPLE 6a

Oxidation Dyeing Combined with Permanent Waving

A permanent wave was performed on medium-heavy hair which had a basic tone of dark gold blond and whose hair lengths and ends were faded.

The permanent wave was performed according to instructions up to and including the first fixing on the curler.

For the second fixing and simultaneous dyeing, the curlers were removed and 20 ml of paste dye of the formula given below for the color "Cyclamen" with the addition of 0.0004% of magnesium acetate was mixed with 40 ml of a permanent wave fixer with an $H_2O_2$ content of 2%.

The resultant hair dye with a pH of 6.8 was then applied to the hair with an applicator bottle and with a sponge and allowed to work for 10 minutes. As a result, a recoloring of the hair to a red-violet (cyclamen) color tone was obtained in addition tot he permanent wave. The time of action can be varied between 5 and 15 minutes according to the desired color intensity.

| Formula for "Cyclamen" Paste Dye | |
|---|---|
| Cetyl stearyl alcohol | 10.0 g |
| Coconut fatty acid monethanolamide | 2.0 g |
| Stearic acid monoethanolamide | 2.0 g |
| Stearic acid diethanolamide | 1.0 g |
| p-Toluylenediaminesulfate | 0.5 g |
| p-Amino-o-cresol | 0.4 g |
| p-Aminophenol | 0.1 g |
| Monoethanolamine | 0.2 g |
| Ammonium chloride | 0.2 g |
| Sodium lauryl sulfate | 0.3 g |
| Magnesium acetate | 0.0004 g |
| Sodium sulfite | 0.25 g |
| Ethylenediaminetetraacetic acid | 0.2 g |
| Perfume | 0.2 g |
| Softened water to make | 100.00 g |

EXAMPLE 6b

Oxidation Dyeing Combined With Permanent Wave

A permanent wave was given to medium-heavy hair which had a basic dark gold blond color and whose lengths and ends had faded.

The permanent wave was performed according to instructions for its application, up to and including the first fixing on the curler.

For the second fixing and simultaneous dyeing the curlers were removed and 20 ml of paste dye of the formula given below for the color, "Mahogany," with the addition of 0.0004% of magnesium acetate, was mixed with 40 ml of a permanent-wave fixer with a hydrogen peroxide content of 2%.

The resultant hair dye with a pH of 6.8 was then applied with an applicator bottle and a sponge and allowed to act for 10 minutes. The result was a recoloring of the hair to a strong red in addition to the permanent wave The time of action can be varied between 5 and 15 minutes according to the desired intensity of color.

| Formula for the "Mahogany" Paste Dye | |
|---|---|
| Cetyl stearyl alcohol | 10.0 g |
| Coconut fatty acid monoethanolamide | 2.0 g |
| Stearic acid monoethanolamide | 2.0 g |
| Stearic acid diethanolamide | 1.0 g |
| p-Toluylenediamine sulfate | 0.4 g |
| p-Aminophenol | 0.4 g |
| p-Amino-o-cresol | 0.4 g |
| o-Nitro-p-phenylenediamine | 0.4 g |
| Monoethanolamine | 0.2 g |
| Ammonium chloride | 0.2 g |
| Sodium lauryl sulfate | 0.3 g |
| Magnesium acetate | 0.0004 g |
| Sodium sulfite | 0.25 g |
| Ethylenediaminetetraacetic acid | 0.2 g |
| Perfume | 0.2 g |
| Softened water to make | 100.00 g |

Experiments have shown that, in addition to the potassium iodide used in Examples 1a to 3a, the alkali metal salts, potassium bichromate and lithium chloride, and, in addition to the magnesium acetate cited in Examples 4a to 6a, the alkali metal salts, potassium chloride and barium nitrate, when used as additives to hair dyes, have the effect of permitting a brilliant and intensifying recoloring or freshening of the color of the treated hair, even in the case of a formula that has been acidified and thus is more gentle on the hair.

We claim:

1. An agent for dyeing human or animal hair, comprising: a mixture of approximately one-third by weight of an oxidation dye in creme or gel form containing an effective amount of an oxidation dye and approximately two-thirds by weight of a developer solution containing approximately two percent of hydrogen peroxide, and as a catalyst 0.0001 to 1.00 per cent by weight of at least one salt selected from the group consisting of potassium iodide, potassium bichromate, lithium chloride, magnesium acetate, calcium chloride and barium nitrate, said agent having a pH between 5.9 and 6.9.

2. An agent according to claim 1, wherein the percentage of the catalyst is between 0.0004 and 0.0001.

3. A method of preparing a dyeing agent for human or animal hair, comprising the steps of: mixing approximately one-third by weight of an oxidation dye in creme or gel form containing an effective amount of an oxidation dye, and approximately two-thirds by weight of a developer solution containing approximately two percent of hydrogen peroxide, and 0.0001 to 1.00 percent by weight of a catalyst with the oxidation dye before the addition of the developer solution, said catalyst being at least one salt selected from the group consisting of potassium iodide, potassium bichromate, lithium chloride, magnesium acetate, calcium chloride and barium nitrate, so as to result in a dyeing agent having a pH between 5.9 and 6.9.

4. A method of preparing a dyeing agent for human or animal hair, comprising the steps of: mixing approximately one-third by weight of an oxidation dye in creme or gel form containing an effective amount of an oxidation dye, and approximately two-thirds by weight of a developer solution containing approximately two percent of hydrogen peroxide, and 0.0001 to 1.00 percent by weight of a catalyst simultaneously with the mixing of the oxidation dye with the developer solution, said catalyst being at least one salt selected from the group consisting of potassium iodide, potassium bichromate, lithium chloride, magnesium acetate, calcium chloride and barium nitrate, so as to result in a dyeing agent having a pH between 5.9 and 6.9.

5. A method of preparing a dyeing agent for human or animal hair, comprising the steps of: mixing approximately one-third by weight of an oxidation dye in creme or gel form containing an effective amount of an oxidation dye, and approximately two-thirds by weight of a developer solution containing approximately two percent of a hydrogen peroxide, and 0.0001 to 1.00 percent by weight of a catalyst immediately after the mixing of the oxidation dye with the developer solution, said catalyst being at least one salt selected from the group consisting of potassium iodide, potassium bichromate, lithium chloride, magnesium acetate, calcium chloride and barium nitrate, so as to result in a dyeing agent having a pH between 5.9 and 6.9.

6. A method according to any one of claims 3 to 5, wherein the percentage of the catalyst is between 0.0004 and 0.0001.

7. A method of dyeing human or animal hair, comprising the steps of: preparing a dyeing agent having a pH between 5.9 and 6.9, from a mixture of approximately one-third by weight of an oxidation dye in creme or gel form containing an effective amount of an oxidation dye, and approximately two-thirds by weight of a developer solution containing approximately two percent of hydrogen peroxide, and 0.0001 to 1.00 percent by weight of at least one salt selected from the group consisting of potassium iodide, potassium bichromate, lithium chloride, magnesium acetate, calcium chloride and barium nitrate as a catalyst; immediately thereafter applying said dyeing agent to the hair and letting the same act on the hair for a period of time sufficient to dye the hair; and washing the dyeing agent out of the hair.

8. A method of re-dyeing human or animal hair which in natural state is dark and has previously been dyed to a lighter state, comprising the steps of: applying a first, conventional alkalinely adjusted hair dyeing agent to recent growth of darker hair close to the scalp, preparing a second dyeing agent having a pH between 5.9 and 6.9, from a mixture of approximately one-third by weight of an oxidation dye in creme or gel form containing an effective amount of an oxidation dye, and approximately two-thirds by weight of a developer solution containing approximately two percent of hydrogen peroxide, and 0.0001 to 1.00 percent by weight of potassium iodide, potassium bichromate, lithium chloride, magnesium acetate, calcium chloride and barium nitrate as a catalyst; immediately thereafter applying said second dyeing agent to the lighter state hair adjacent to the recent growth hair and letting the same act on the lighter state hair for a period of time sufficient to dye the hair; and washing both dyeing agents out of the hair.

9. A method of waving and dyeing human or animal hair, comprising the steps of: applying a conventional permanent-wave preparation to the hair, which has previously been washed and wound on curlers, for a given period of time, washing out the hair, fixing the hair, still would on the curlers, with a conventional liquid oxidizing fixing agent; removing the curlers, and re-fixing the hair with a dyeing agent having a pH between 5.9 and 6.9, from a mixture of approximately one-third by weight of an oxidation dye in creme or gel form containing an effective amount of an oxidation dye, and approximately two-thirds by weight of a developer solution containing approximately two percent of hydrogen peroxide, and 0.0001 to 1.00 percent by weight of potassium iodide, potassium bichromate, lithium chloride, magnesium acetate, calcium chloride and barium nitrate as a catalyst; letting the dyeing agent act on the hair for a period of time sufficient to dye the hair, and washing the dyeing agent out of the hair.

10. A method according to any one of claims 7 to 9, wherein the percentage of the catalyst is between 0.0004 and 0.001.

* * * * *